United States Patent [19]

Horz et al.

[11] 4,336,816
[45] Jun. 29, 1982

[54] DEVICE FOR CLEANING SMALL OBJECTS, ESPECIALLY DENTURES

[75] Inventors: Eberhard Horz, Glashutten; Robert Wirsing, Neu Isenburg; Gunter Hoffmann, Hofheim, all of Fed. Rep. of Germany

[73] Assignee: Braun Aktiengesellschaft, Kronberg, Fed. Rep. of Germany

[21] Appl. No.: 190,783

[22] Filed: Sep. 25, 1980

[30] Foreign Application Priority Data

Nov. 10, 1979 [DE] Fed. Rep. of Germany ... 7931846[U]

[51] Int. Cl.³ ............................................. B08B 3/06
[52] U.S. Cl. ..................... 134/110; 134/92; 134/188
[58] Field of Search .............. 134/92, 110, 137, 184, 134/188

[56] References Cited

U.S. PATENT DOCUMENTS

| 1,938,254 | 12/1933 | Hinson | 134/110 X |
| 2,889,836 | 1/1959 | Maley | 134/110 |
| 3,421,528 | 1/1969 | Gomez et al. | 134/188 |

FOREIGN PATENT DOCUMENTS

| 199276 | 6/1908 | Fed. Rep. of Germany | 134/92 |
| 244979 | 2/1979 | Fed. Rep. of Germany | |
| 1169417 | 11/1969 | United Kingdom | 134/188 |

Primary Examiner—Robert L. Bleutge
Attorney, Agent, or Firm—Raymond J. De Vellis

[57] ABSTRACT

A device for cleaning small objects, such as dentures, in a tank containing cleaning fluid is provided. The cleaning fluid is electromagnetically agitated. A removable basket having a perforated bottom is positioned in the tank. Releasably coupled to the bottom of the basket is a basket insert which also contains a perforated bottom. A removable screen is mounted between the basket and basket insert.

9 Claims, 1 Drawing Figure

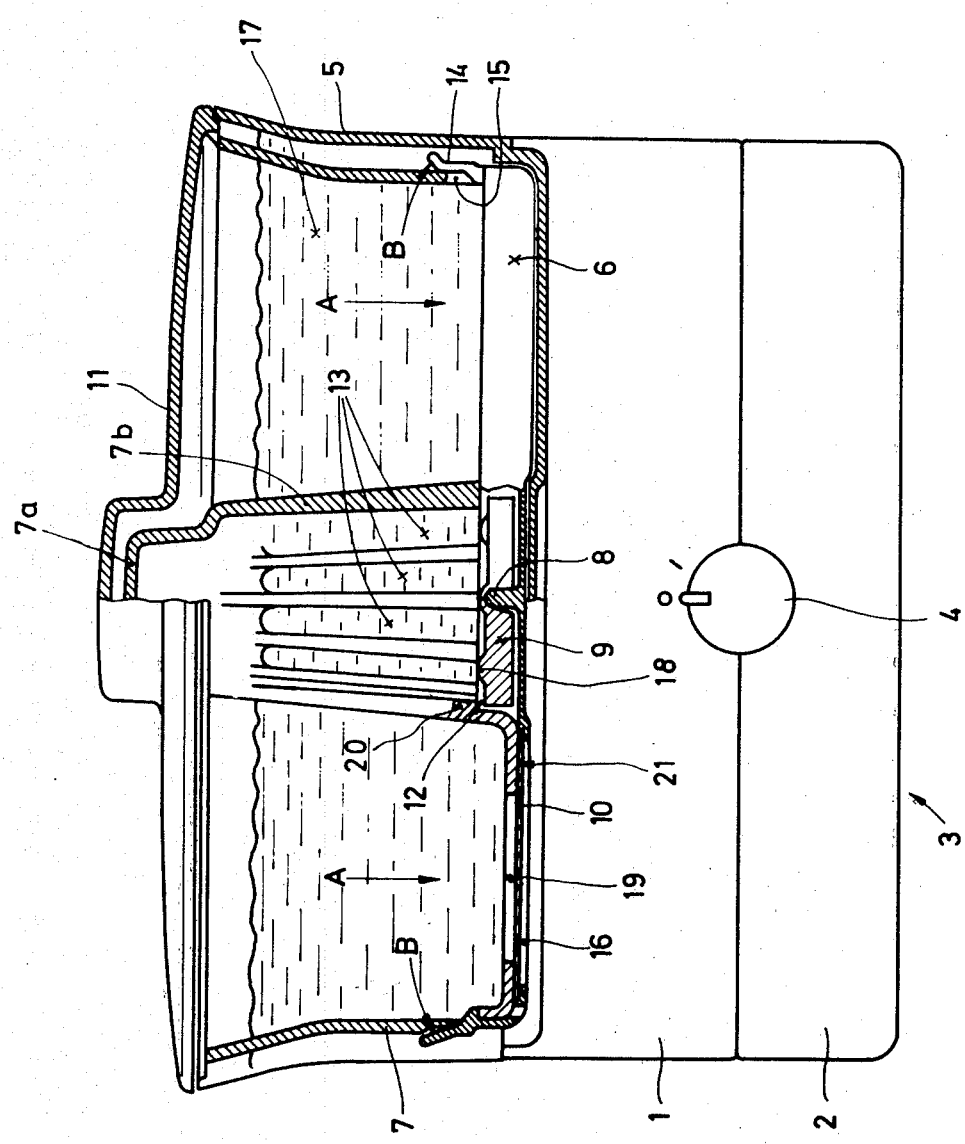

DEVICE FOR CLEANING SMALL OBJECTS, ESPECIALLY DENTURES

BACKGROUND OF THE INVENTION

This invention relates to a device for cleaning small objects, especially dentures, with a tank containing a cleaning fluid. An agitating disc is rotatably mounted in the tank. A motor is located in a base beneath the tank and includes a coupling disc of a magnetic material.

German Utility Model No. 74 34 605 illustrates a cleaning bath for removable dentures. The bath consists of a tank to hold a fluid with a basket-shaped insert suspended in the tank. The insert is perforated in a sieve-like manner. A magnetically influenceable agitator is mounted to be freely movable inside the tank. The agitator is rotated by a device located beneath the tank which produces a magnetic field. In this device, the denture rests upon the basket-shaped insert inside the tank above the magnetically-influenceable agitator so that the cleaning fluid can rinse all parts of the denture. The agitator itself is mounted on a vertical shaft which in turn is mounted on the bottom of the tank.

In another device of this type (United Kingdom Pat. No. 1,169,417), a disc-shaped vibrator made of thin sheet metal is permanently attached to the bottom of the tank for the cleaning fluid. The vibrator is vibrated by an electromagnet in the base of the unit. The dentures rest on a disc-shaped screen above the vibrator. The screen includes a handle to lift the screen out of the tank with the dentures resting atop it.

A denture cleaner is also known (U.S. Pat. No. 3,421,528) in which an agitating disc, made of magnetic material, is rotatably mounted on a pin. The pin is fastened to the bottom of the tank. The denture is placed in a basket having a handle. The basket has an opening in the vicinity of the agitator disc through which an axial extension of the agitator disc extends upward. The axial extension of the agitator disc is provided with ribs which are designed to ensure that the liquid flows especially intensively over all sides of the denture.

These known devices have the disadvantage that the food residues and other particles which are washed off the dentures continue to float around in the cleaning bath after cleaning is complete, so that the cleaning fluid must be replaced often.

The present invention is designed to provide a denture cleaner with electromagnetic agitation, wherein the cleaning fluid can be used comparatively frequently, and the denture is removable from the cleaning tank without the operator's hand coming in contact with the aggressive cleaning fluid. Further, the foreign particles, which are rinsed off, are removable from the tank without decanting the fluid into another container. Thus, fine filtration of the cleaning fluid is provided without having a disadvantageous effect upon the intensive rinsing of the dentures.

SUMMARY OF THE INVENTION

Briefly stated, and according to an aspect of this invention, an improved device for cleaning small objects, such as dentures, is achieved by providing an insert to accept the denture which is rinsed by the cleaning fluid. The insert consists of an essentially cylindrical basket with side walls and a perforated bottom and a basket insert which has openings and is connectable to the basket. The basket insert contains a filter screen and is mountable beneath the bottom of the basket, to the latter.

Advantageously, the basket insert is provided with a pin which serves to mount the agitating disc between the basket insert and the bottom of the basket.

Advantageously, the bottom of the basket has a dome-shaped depression in the vicinity of the agitator disc which extends above the latter. The walls of the depression are provided with slots or similar openings.

In order to facilitate removal of the basket insert from the basket, the basket is provided with slots, grooves, or openings into which the basket insert is lockable by means of spring-loaded tongues, pins, or retaining fingers.

In order to prevent the agitator disc from slipping off the bearing pin during operation, the basket is provided with ribs or projections in the vicinity of the depression. The ribs or projections extend horizontally and have the upper surface of the agitator disc abutting them.

The filter screen is advantageously inserted in the gap between the basket and the basket insert. The gap is set so that the foreign particles collect above the filter screen, but beneath the bottom of the basket.

BRIEF DESCRIPTION OF THE DRAWING

The invention both as to its organization and principles of operation, together with further objects and advantages thereof, may be better understood by referring to the following detailed description of an embodiment of the invention taken in conjunction with the accompanying drawing showing a partial lengthwise section through a denture cleaner, in accordance with this invention.

The denture cleaner consists essentially of a base 3, which contains an electric motor (not shown) and a magnet (also not shown) driven by the motor in a manner well known in the art. An on-off switch 4 is also provided. A removable tank 5 holds a cleaning fluid 17, a basket 7, with a basket insert 6 clipped thereto, an agitator disc 9, a filter screen 10, which is inserted between the basket 7 and the basket insert 6, and a cover 11 which covers the tank 5. The basket insert 6 includes a perforated bottom or openings 16 and is positioned under the bottom 21 of the basket 7. The filter screen 10 is mounted between the perforated bottom or openings 19 of the basket 7 and the perforated bottom or openings 16 of the basket insert 6. The filter screen 10 may be mounted in a plurality of ways such as a snap fit arrangement onto the basket insert 6 by means of bumps or projections located on the basket insert 6.

When the motor, located in the base 3 which is made up of housing shells 1 and 2, is turned on by the switch 4, the agitator disc 9 begins to rotate. This sets the cleaning fluid 17 moving by means of blades or bumps 18 associated with the agitation disc 9. Thus the cleaning fluid 17 rinses and thereby cleans the dentures (not shown) lying in the basket 7. After cleaning is complete, the cover 11 is removed. Then the basket 7, with the basket insert 6 and filter screen 10, is removed from the tank 5. The basket 7 is raised out of the cleaning fluid 17 by the user grasping the dome-shaped part 7a of the basket 7. The cleaning fluid 17 is left behind in the tank without any foreign particles therein. When the basket 7 is removed, the fluid flows downward through openings 19 in the bottom of basket 7, the direction of arrow A. This causes the foreign particles to collect on top of the filter screen 10 which is disposed beneath the bottom 21 of the basket 7.

The filter screen 10 can easily be replaced by bending spring loaded tongues, pins or retaining finger 14 in the direction of arrow B until the retaining catch comes out of slots or grooves such as openings 15 and basket insert 6 is released so that it can be pulled down and off the basket 7. A clean filter screen 10 can then be inserted in the narrow annular depression in the basket insert 6.

When the agitator disc 9 threatens to slide up and off a bearing pin 8, a top edge 12 of the agitator disc 9 abuts horizontally extending projections or ribs 20. The ribs 20 are provided on the dome-shaped part 7b, near the bottom of the basket 6. The walls of the dome-shaped part 7b extending generally above the agitation disc 9 are provided with slots 13 or the like to provide proper fluid communication, as is well known in the art. The bearing pin may be integrally formed with the basket insert 6. When the bearing pin 8 is worn, it is merely necessary to replace the basket insert 6. It is within the scope of this invention to form the bearing pin 8 integral with the filter screen 10. Further, the bearing pin 8 and the filter screen 10 may both be integrally formed with the basket insert 6.

The agitation disc 9 is provided on its upper surface with a plurality of hemispherical bumps 18 to cause fluid agitation, as is well known in the art. Otherwise, the agitation disc 9 presents a flat, disc-shaped body of rotation.

While an embodiment and application of the invention has been shown and described, it will be apparent to those skilled in the art that many more modifications are possible without departing from the inventive concepts herein described. The invention, therefore, is not to be restricted except as is necessary by the prior art and by the spirit of the appended claims.

What is claimed as new and desired to be received by Letters Patent of the United States is:

1. A device for cleaning small objects in a tank capable of containing a cleaning fluid and provided with electromagnetic agitation comprising:

a substantially cylindrical removable basket having side walls and a perforated bottom positioned in the tank;

basket insert means having a perforated bottom and being releasably connectable to said basket, said basket insert means including a bearing pin and the electromagnetic agitation for the device is made up of an agitator disc rotatably mounted in the tank and a motor below the tank including a coupling disc of a magnetic material for electromagnetically engaging said agitator disc, said bearing pin serving as a bearing for said agitator disc; and filter screen means mountable between said perforated bottom of said basket and said perforated bottom of said basket insert.

2. The device as in claim 1 wherein said removable basket includes a dome-shaped member having rib means proximate said agitator disc and horizontally extending above said agitator disc to prevent said agitator disc from sliding up and off said bearing pin.

3. The device as in claim 1 wherein said side walls of said basket include openings and said basket insert is provided with retaining fingers to releasably secure said basket insert in said openings.

4. The device as in claim 1 wherein said filter screen means is mounted between said basket and said basket insert so that foreign particles collect above said filter screen means but beneath the bottom of said basket.

5. The device as in claim 1 wherein said bearing pin is integrally formed as part of said basket insert.

6. The device as in claim 1 wherein said agitator disc includes on its upper surface a plurality of hemispherical bumps.

7. The device as in claim 1 wherein said filter screen means is snap-mounted into said basket insert.

8. The device as in claim 1 wherein said bearing pin is integrally formed as part of said filter screen means.

9. The device as in claim 1 wherein said bearing pin and said filter screen means are integrally formed as part of said basket insert.

* * * * *